US007666357B2

(12) United States Patent
Sattler et al.

(10) Patent No.: US 7,666,357 B2
(45) Date of Patent: Feb. 23, 2010

(54) SYSTEM FOR AUTOMATIC OPENING OF REAGENT VESSELS

(75) Inventors: Stephan Sattler, Stamberg (DE); Heiko Dorn, Mannheim (DE); Gottfried Senftner, Lampertheim (DE); Hermann Erb, Fussgoenheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 760 days.

(21) Appl. No.: 10/778,586

(22) Filed: Feb. 13, 2004

(65) Prior Publication Data

US 2004/0241864 A1 Dec. 2, 2004

(30) Foreign Application Priority Data

Feb. 27, 2003 (DE) ................. 103 08 362

(51) Int. Cl.
*B01L 3/00* (2006.01)
(52) U.S. Cl. ...................................... 422/99
(58) Field of Classification Search .................. 422/63, 422/65, 67, 99, 100, 102, 104; 436/43, 47, 436/48, 49, 51, 174, 180, 183, 807, 809, 436/810; 81/3.07, 3.2, 3.36, 3.4; 435/288.1; 294/88; 29/273; 220/23.4; 206/221; 215/227
See application file for complete search history.

(56) References Cited

U.S. PATENT DOCUMENTS 3,830,390 A * 8/1974 Gach .......................... 215/220
3,991,896 A 11/1976 Miranda ...................... 215/227
4,312,695 A * 1/1982 Willis ........................... 81/3.2
4,876,926 A * 10/1989 Muszak ........................ 81/3.2
5,064,059 A 11/1991 Ziegler et al. ............... 206/221
5,145,646 A 9/1992 Tyranski
5,413,152 A * 5/1995 Burrows ...................... 141/18
5,846,489 A 12/1998 Bienhaus et al. ............. 422/63
5,862,934 A 1/1999 Sattler et al. ............... 220/23.4
6,216,340 B1 * 4/2001 Fassbind et al. .............. 29/773
6,255,101 B1 7/2001 Rousseau et al. ......... 435/288.1
6,398,281 B1 6/2002 Heimberg .................... 294/88
2004/0067169 A1 4/2004 Krause

FOREIGN PATENT DOCUMENTS

DE        EP 0504967    3/1992
DE        EP 0692308    7/1995
DE        EP 0930504    1/1999
EP           383564 A2 * 8/1990
WO        WO 83/01912   6/1983
WO        02062474 A2   8/2002

* cited by examiner

*Primary Examiner*—Walter D Griffin
*Assistant Examiner*—Bobby Ramdhanie
(74) *Attorney, Agent, or Firm*—Dinsmore & Shohl LLP

(57) ABSTRACT

The invention relates to an analysis system which, by means of a reagent cartridge opening module, permits automatic opening of reagent vessels which are closed by screwing. The reagent cartridge opening module for this purpose has catch elements which can lock securely against rotation in correspondingly configured catch elements of a reagent vessel lid. In addition, the reagent cartridge opening module and the reagent vessel lid are connected via snap-in elements, so that transport of the reagent vessel lid perpendicular to the plane of the rotational movement is possible.

26 Claims, 7 Drawing Sheets

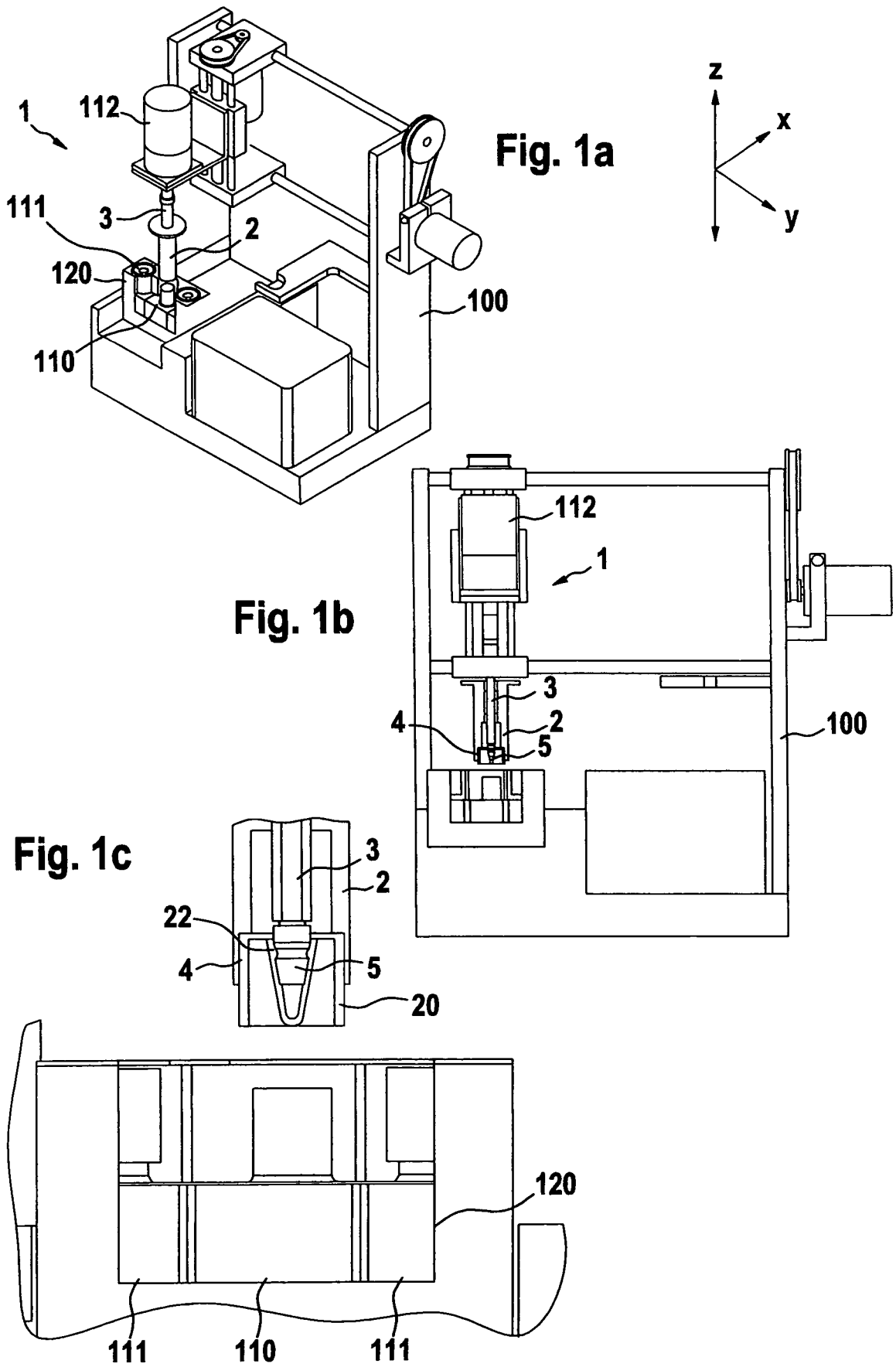

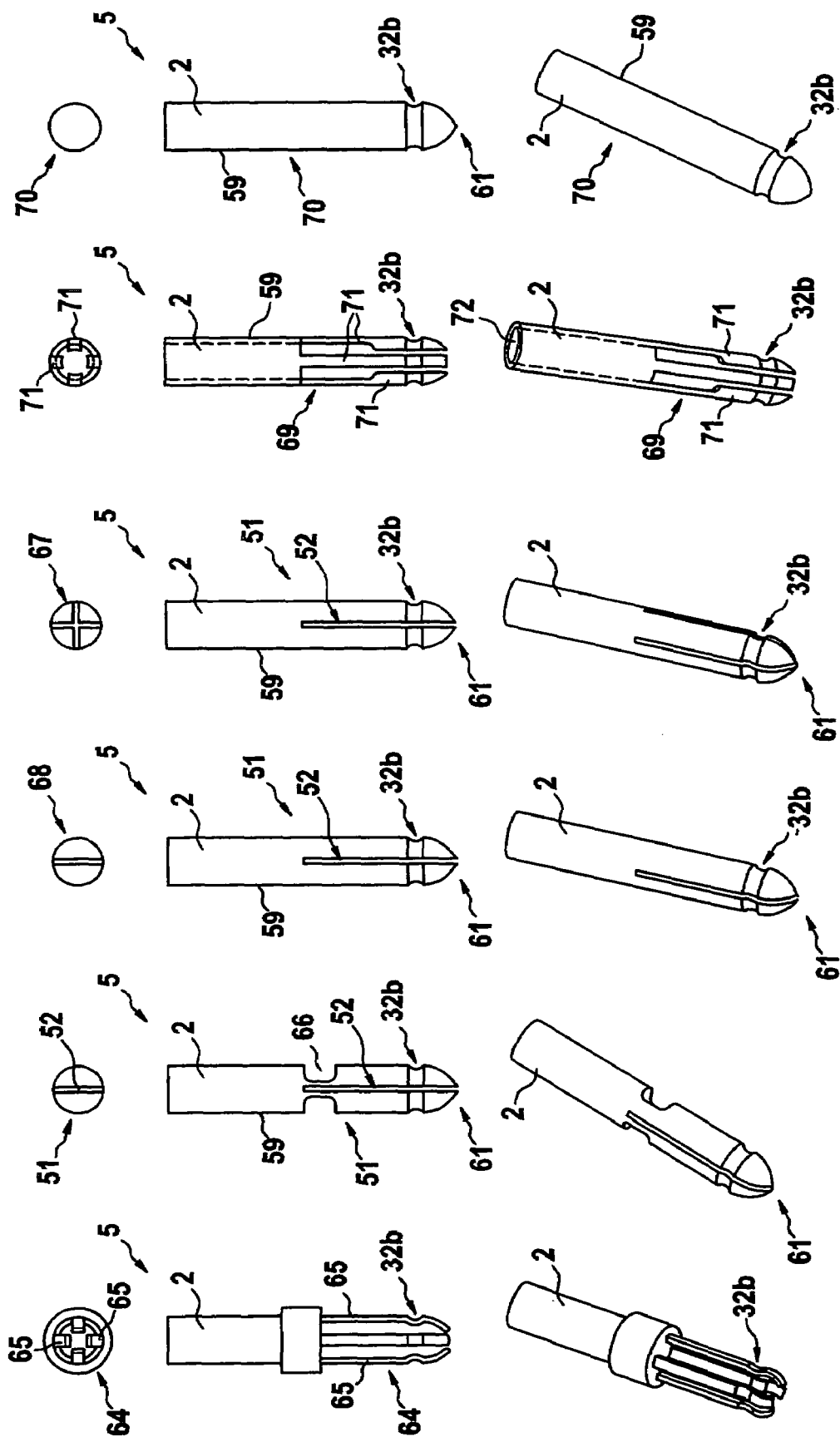

SYSTEM FOR AUTOMATIC OPENING OF REAGENT VESSELS

FIELD OF THE INVENTION

The invention relates to the technical field of automatic analysis devices in which a large number of reagents can often be simultaneously accommodated and processed. In this connection, it is desirable to permit, as far as possible, fully automatic handling of samples and reagents in the analysis devices so that no manual handling steps are necessary. This makes it possible to simplify and accelerate many analysis procedures, and mistakes due to human error during the analysis procedure can be minimized.

BACKGROUND OF THE INVENTION

Stringent demands are placed on automatic analysis devices, especially in large-scale laboratories in which a high sampling rate must be permitted. Here, the analysis devices must be able to deal with a large number of reaction vessels with different samples and must be able to allocate these to different reagent containers. In this connection, pipetting devices, inter alia, are used to permit analysis of a sample by addition of the corresponding reagents and also further sample processing steps. Thus, with fully automatic treatment of reagents and samples, even labour-intensive analysis procedures can be performed reliably and quickly without requiring the involvement of specialized personnel for specialized analysis procedures. A demand placed on a fully or partially automated analysis procedure is, for example, the handling of sample quantities of different sizes which require a corresponding quantity of reagents. A fully automatic analysis system has to satisfy a wide variety of requirements. There are analysis systems with a high throughput and others with a low throughput, as are outlined in brief below.

In analysis systems for low throughputs of reagents, the cycle time for liquid removal is approximately 4 to 10 seconds, with the pipetting needle piercing the vessel lid upon each removal. The reagent cartridge has a relatively long dwell time on the device because of the low throughput. The dwell time is extended still further if the reagent cartridge contains seldom used reagents which are not often called upon and which accordingly can remain for up to 4 weeks in the analysis system with low throughputs. In these reagent cartridges, there is a need for a high level of protection against evaporation.

In analysis systems distinguished by a high throughput of reagents, there is generally a short cycle time of between 1 and 4 seconds for the pipetting and the positioning of reagent rotor and pipetting needle. Because of the short cycle time, piercing of the funnels with the pipetting needle is not possible. Because of the high throughput of reagents, the dwell time of the respective reagent cartridges on such analysis systems is only one to two days, for which reason evaporation from an opened flask can be tolerated here.

The handling of very small volumes is described, for example, in EP 0 504 967. Said document discloses reagent containers which permit the removal of small volumes and in which evaporation or aging of the remaining fluid in the container during further processing steps is avoided.

For this purpose, the reagent container has a suitably designed lid which, on one hand, is suitable for removal of liquid and, on the other hand, suppresses evaporation of the contents of the container. The lid has, in the middle of its base, a circular opening which is directed into the lid interior and opens out in a conical tip. For removing a sample, the tip of the cone is first pierced so that a pipetting needle, which is provided for removing very small sample quantities, can then be introduced into the vessel. When the reagent has been removed from the vessel, a small opening remains exclusively at the tip of the cylinder. After removal of the sample, the small opening at the cylinder tip of the lid also ensures that almost no liquid evaporates from the reagent container and that the content of the vessel does not undergo changes due to contact with, for example, atmospheric humidity or oxygen in the environment. Further details of this vessel closure can be taken from the prior art.

However, if a higher throughput and shorter processing times are to be achieved, the pipetting device, if it is to permit efficient handling of samples, must be equipped with correspondingly large pipetting tips to take up liquid. To ensure that in this case too the larger pipetting tips can still be inserted into the interior of the reagent vessel, a larger opening in the lid would be necessary.

In the prior art, many possible ways are described for producing openings in a closure of a reagent vessel. As is described in patents U.S. Pat. Nos. 6,255,101 and 3,991,896, this can be done by means of a ball being pushed through the shaft of a reagent vessel lid with the aid of a pin. The ball is pushed into the interior of the reagent container so that reagent liquid can then be removed through the shaft. Other possibilities, for example piercing a closure cap by means of a cannula as in document WO 83/01912, are likewise conceivable. The diameter of the opening can be chosen according to the size of the shaft or the cannula.

An alternative to an enlarged opening in a reagent closure involves removing the lid of the reagent containers prior to use.

In the prior art, this type of sample handling is used, for example, in analysis systems in the field of clinical-chemical analysis of biological samples. To remove a desired quantity of liquid reagent, the reagent is removed from the open reagent container and is transferred by means of an automatic pipetting device into a reaction cuvette. For each pipetting procedure, an electromechanically driven arm of the pipetting device is guided to an open reagent container so that handling of samples can take place in the desired manner. The content of a standard reagent container in this case suffices for a large number of pipetting procedures. In this connection, it has been found that fluid evaporates during the analysis method before it can be completely used up, on one hand through the removal of the reagent closure and on the other hand through the creation of a large opening in a closure cap. Especially in rooms with low atmospheric humidity, considerable amounts of the reagent solution are often lost through evaporation. One consequence of this is that the evaporation causes an increase in the concentration of the reagent in the fluid. By contrast, the volume of the reagent solution increases when using open reagent containers in rooms with relatively high atmospheric humidity, or through condensation water forming when cooled reagents are used so that the reagent concentration decreases over the course of time. Moreover, when open reagent containers are used, there is an exchange of gas with the surrounding air, which among other things causes aging of a reagent. Such effects on the reagent, in particular on the reagent concentration, result in a deterioration in the analysis precision. It has additionally been found that a removal of the reagent closure often has to be done manually. Under these circumstances, the laboratory personnel must take new reagent containers from their packaging and first of all remove the closure in order then to place the open reagent container in the analysis system in place of an empty reagent container. Since it often happens that many different reagents are needed at different times in one and the same analysis system, manual handling by laboratory personnel requires considerable labor. When reclosing the containers, it must additionally be ensured that the closures are not mixed up. In procedures carried out manually, the possible confusion of the closures represents a source of uncertainty.

In the prior art, therefore, methods are described which permit automatic removal of a reagent container closure. The document EP 0 930 504 discloses a lid-gripping device which is intended for automatic handling of a lid on sample vessels. The lid of the sample vessels in this case has a spike around which the lid-gripping device can grip. By means of a chuck, the lid is held so securely that, when the lid-gripping device is lifted, the lid is completely detached from the vessel, while a holding-down sleeve holds the vessel down to prevent lifting of the vessel.

The document U.S. Pat. No. 5,846,489 likewise discloses an automatic system for opening reagent vessels. Here, a pin of a gripping device is inserted into a groove provided for this purpose in the lid. At one end, the pin has a bead which allows the pin to be clamped in the groove of the lid. The lid can then be removed from the reagent vessel by lifting the pin.

Moreover, in U.S. Pat. No. 5,064,059, a device is described which allows a lid to be removed from the reagent vessel. However, the prior art described discloses only an automatic opening of reagent vessels closed by a stopper. Usually, stoppers are only used to close test tubes in which, for example, blood or another liquid from the human or animal body is received, but not reagent vessels. A disadvantage of the prior art is in this case that the mechanisms described do not permit opening of a screw-type closure of a reagent vessel. In practice, however, it has been found that, for reagent vessels which often contain a volatile fluid, a screwable closure is particularly suitable since such a screw-type closure guarantees a reliable sealing of the vessel.

In the prior art, U.S. Pat. No. 6,216,340 describes the removal of a reagent closure which is secured on the vessel by screwing. In this case, opener and reagent lid interact in the manner of a bayonet closure. Through a guide groove formed in the reagent closure, the automatic opener can insert a pin along the guide groove by rotation into the lid until this is mounted against a limit stop of the guide groove. If the rotational movement is continued in this direction, turning the lid off from the reagent vessel is possible. By rotating the opener in the opposite direction, the connection between lid and opener is released again. A disadvantage of the prior art is the fact that a precise production of the bayonet closure on the lid is an essential requirement for ensuring the functional reliability of the system. The screwing operation, after filling of the vessel, must guarantee a narrowly tolerated angle position of the bayonet closure and also have a good sealing effect.

Moreover, the opener must be guided with precision to the respective reagent vessel to permit engagement of the pin of the opener in the bayonet closure. This requires either a precise placement of the reagent vessels in the analysis system or a detection of position by the analysis system for the respective reagent vessel. Moreover, complex tools are needed for producing the reagent lid, with the result that the production costs are increased. Particularly in the case of reagent vessels handled as disposable articles, this is a considerable disadvantage. Before the opener, after removal of a first lid, can be used again to open reagent vessels, the lid additionally has to be removed from the opener. In the example described, additional measures are needed to do this, which measures permit rotation of the lid in the opposite direction so that the lid can be removed from the opener.

SUMMARY OF THE INVENTION

The object of the invention is to eliminate the disadvantages of the prior art. This is to be done by permitting automatic opening of reagent vessels in an analysis device by means of unscrewing, without having to make extensive demands on the method sequences in the analysis device and on the system itself. The invention therefore has the object of making available a system for opening reagent vessels, and also suitable reagent vessels, with a screwable closure as such, with which said aims are achieved.

The invention includes a system and a method for opening reagent vessels. The system has a carrier and a centering unit which is essentially guided inside the carrier. At a lower end of the carrier there is a catch element which is so configured that it can lock securely against rotation in a lid provided for this purpose. If the catch element of the carrier is then turned, the movement of the catch element causes a rotational movement of the lid, so that a screw connection can be released. By contrast, the centering unit has, at a lower end, a snap-in element which can engage in a snap-fit connection with a lid provided for this purpose. Before the locking of the catch elements in a lid that is to be opened, the centering unit advantageously first engages in a snap-fit connection. When the centering unit is connected to the lid in this way, the existing snap-fit connection indirectly permits a relative positioning of the carrier with respect to the vessel lid and thus easy guiding of the catch elements to one another. The catch element of the carrier can now lock correspondingly into a catch element of the lid. If a centering of the system is advantageously performed in the described manner, method steps for opening reagent vessels in the analysis system can be simplified, since it is possible to some extent to do without a precise guidance of the opener to the reagent vessel, in particular of the respective catch elements to one another. The described preliminary centering of the system consequently also makes it possible to use catch elements of small size without greater demands having to be placed in particular on the method sequence. When the lid is connected to the snap-in element and the latter is unscrewed from the reagent vessel by means of a rotational movement, the detached lid can be transported away from the reagent vessel by means of a movement of the snap-in element which is essentially perpendicular to the plane of the rotational movement, in which process the lid remains clinging to the snap-in element.

The invention further includes reagent vessels with a screwable lid, which reagent vessels can be opened with a system according to the invention. For this purpose, the reagent vessels comprise a vessel with a vessel neck which has a thread. The reagent vessels can be connected to a lid by screwing and are closed by said lid. The lid comprises a jacket in the form of a hollow cylinder which, on its inside, has a thread which interacts with the thread on the vessel neck in such a way that a snap-fit connection between lid and reagent vessel is permitted. Sealing between lid and reagent vessel is achieved with the aid of a sealing lip.

The hollow cylinder formed by the jacket is closed by a cover plate on the top face of the hollow cylinder, so that the lid remains open towards its bottom face and can be turned over the vessel neck. The lid also has a snap-in element and a catch element. The elements are so configured that they can engage in a snap-fit connection with a system for opening reagent vessels and lock securely against rotation in the system.

The system for opening reagent vessels is advantageously used in an analysis system. Here, the analysis system has at least one drive unit which drives the catch element of the carrier so that this turns. With the aid of the same drive unit or another drive unit, a linear movement of the centering unit is effected which is essentially perpendicular to the plane of the rotational movement. One or more control units in the analysis system match the movement of the carrier and of the centering unit to one another so that a closure of a reagent vessel can be unscrewed and the lid can be transported away from the reagent vessel.

The invention permits automatic opening of a reagent vessel closed with a screw-type closure. In this respect, the invention is distinguished by a simple operating procedure involving the use of catch elements and snap-in elements in the system. By assigning the movement patterns, namely a rotational movement, and a linear movement essentially perpendicular to the latter, to separate elements of the opener (carrier and centering unit), considerable simplifications in the structure of the opener and in the operating procedure are made possible. According to the invention, a snap-fit connection, allowing the lid to cling to the centering unit and thus permitting transport of the lid, is realized separately from the rotationally secure connection of the lid to the carrier. In this way, it is possible, for example, to use simple and robust catch elements and snap-in elements which, particularly as used in the vessel lid, permit economical production of the vessel closure.

In the context of the invention, the term locking is to be understood as any form of rotationally secure connection between the catch elements of the carrier and of the reagent vessel lid. For example, a rotationally secure connection can be ensured by the catch elements engaging, abutting, etc., in one another.

In a preferred embodiment, in the operating procedure for opening reagent vessels in the manner described, the opener is first centered relative to the reagent vessel, in which the centering unit snaps into a snap-in element of the cover plate of the reagent vessel closure, before rotationally secure locking takes place between the opener and a reagent vessel. If a snap-in element for the centering unit is provided in the center of the cover plate, and if the carrier is arranged concentrically about the centering unit, the carrier, and thus the catch element arranged on the carrier, is automatically positioned relative to the center of the lid. The catch elements of the carrier and of the lid can in this way engage easily in one another, without exact control of the carrier being required for this.

The catch elements and snap-in elements can take various forms. It has been found that quite simple configurations permit a rotationally secure locking and secure connection of the respective elements. In an advantageous embodiment, the cover plate of the closure is provided with a snap-in element in the form of a depression which ends in a tapered cone directed into the interior of the lid. A depression formed in this way, as has already been described in the prior art in the document EP 0 504 967, facilitates insertion of a corresponding snap-in element of the centering unit into the reagent vessel lid.

To further adapt a depression, as described, to a snap-in element of an opener, it has proven advantageous that the depression, in its upper area, has a protuberance, for example in the form of a ring, which projects into the interior of the hollow space formed by the depression. A corresponding snap-in element of the opener has a corresponding notch into which the ring of the depression can snap. It is of course also conceivable for notches to be present inside the depression and for the snap-in element of the opener to correspondingly have a convex shape. In practice, however, it has been found that a concave shape of the snap-in element of the opener and a corresponding convex shape of the snap-in element of the lid are easier to handle, since in this way it is possible to achieve a more favourable distribution of stresses in the material of the lid. Given the stresses arising in the material, the achieved distribution of stresses permits a snap-fit connection.

A corresponding snap-in element of the opener advantageously has a conical shape. This makes it easier to insert the snap-in element into a depression, as described. When the opener is lowered onto the cover plate, the tapering conical shape of the depression permits an automatic preliminary centering of the snap-in element in towards the center of the depression. Inexactly controlled operating procedures can be compensated for in this way.

Furthermore, it is also conceivable for the snap-in element to be introduced into the depression without said depression having special protuberances or recesses. In this case, the snap-in element is simply clamped within the depression, so that, within the meaning of the invention, connections in which the snap-in element is securely clamped on the lid are also to be understood as snap-fit connections. This clamping can be supported by shaping of the snap-in element, as described. To promote a snap-fit connection, it additionally proves advantageous for the lid to be made of at least two different plastics with different degrees of hardness. Here, for example, the depression is made of a softer plastic than the rest of the lid. The lesser hardness of the plastic makes it easier, at this location, to adapt the depression to the snap-in element of the centering unit and thus achieve a snap-fit connection with the opener, since the material has the required elasticity for this. Because of the elasticity of the depression, repeated insertion of the snap-in element into the depression is also possible, without causing material fatigue which leads to tears or other damage in the lid. The harder outer area of the lid, by contrast, has to withstand the acting torque during screwing and unscrewing of the lid and must do so without deformation, in particular of the catch elements. Repeated screwing and unscrewing of the lid is thus easily made possible.

For the catch elements on the opener and on the lid of the reagent vessel, a number of mutually adapted structures are likewise conceivable. Thus, for example, channels or ribs both on the catch element of the opener and also on the outer wall of the lid jacket are possible, which ensure engagement and rotationally secure locking of the snap-in elements in one another and permit turning of the lid. It is also possible for the catch element of the opener and of the lid to each have toothed structures which engage in one another. The toothed structure of the lid is advantageously formed in the cover plate, so that the catch element of the opener can engage, directly on the cover plate, into the toothed structure of the lid. In a preferred embodiment, the teeth of the respective catch element have a bevel, so that insertion of the teeth in one another is made easier. If the catch element of the lid is integrated into the cover plate, this permits opening of the reagent vessels without the opener having to engage around the jacket of the vessel closure. This minimizes the amount of space taken up by the opener during unscrewing in the analysis system. This proves advantageous especially in analysis systems which use reagent kits inside a cartridge, since in this case there is often no room for engagement of an opener into the cartridge. The system then depends on the opener taking up no space, or only minimal space, inside the cartridge for the purpose of rotationally secure locking. Integration of the opener into conventional analysis systems shows that an advantageous embodiment of this kind fulfills important conditions and satisfies the strict demands on spatial adaptation of reagent cartridge, reagent vessel and analysis system. To satisfy the spatial demands of an analysis system, the size of the reagent vessel and of the closure can also be adapted to correspond to the available space. For example, embodiments are conceivable in which sufficient adaptation is afforded by reducing the diameter of the vessel neck or reducing the thread depth of the vessel neck and lid jacket. Advantageously, a reliable sealing of the contents of the reagent vessel should also be guaranteed.

To permit automatic handling of a large number of reagent vessels, a closure cap, after it has been unscrewed, has to be removed again from the opener. In this connection, it is conceivable for the reagent vessel to be closed again after the fluid has been withdrawn. If the locked connection between lid and opener is maintained during the operating procedure, the lid clinging to the opener can be placed back onto the vessel after the sample has been withdrawn, so that, by a corresponding rotational movement of the carrier, the reagent vessel can be reclosed. The snap-fit connection is then released by means of a movement of the snap-in element away from the reagent vessel, this movement being essentially perpendicular to the plane of the rotational movement. The snap-in element of the centering unit is withdrawn from the lid, and the lid remains on the vessel because of the screw connection. The opener is thus freed again, and the system can be used again to open further vessels. To free the snap-in element of the opener, the reagent container or lid is held down.

This operating procedure proves particularly advantageous when the reagent vessel contains fluids which, upon contact with the surrounding air, rapidly undergo aging effects, or in which the reagent concentration is crucially impaired through condensation, for example of atmospheric humidity, or through evaporation of the fluid. Reclosing of these vessels consequently avoids excessive impairment of the reagents and can be easily realized by the device/method according to the invention.

On the other hand, however, there is also the possibility of discarding the lid after opening the vessel. To do so, the lid must be removed from the carrier, in which case, advantageously, the opener first positions the lid directly over a discard station provided for this purpose. In a preferred embodiment, the centering unit is guided movably inside the carrier, so that the lid can be easily stripped from the opener, as is described in more detail below. For this purpose, the centering unit is moved along its longitudinal axis, while the carrier remains fixed in position in the system. With the lid now clinging to the centering unit, it is moved inside the carrier, by the movement of the centering unit, until the lid is brought up against, for example, a projection provided in the carrier. A continuation of the movement of the centering unit then has the effect that the lid is pressed against the projection until the lid detaches from the snap-in element. The lid can thus be stripped from the centering unit without the need for additional movements or devices in the system.

Moreover, a centering unit guided movably inside the carrier permits an improved positioning of the opener relative to the reagent vessel closure, said positioning being realized particularly easily in this way. A preliminary centering of the carrier by means of a snap-fit connection of the centering unit to the lid, as described, is thus easy to achieve.

In addition, a preliminary centering of the carrier can be achieved if the carrier is designed in the form of an outer sleeve which can be pushed over a partial area of the vessel closure.

For this purpose, the sleeve is initially pushed over a first area of the vessel lid so that a partial area of the vessel closure is surrounded by the sleeve of the carrier. In the inside of the sleeve, the carrier advantageously has catch elements which initially lie on the catch elements of the lid when the sleeve surrounds the first area of the vessel lid. Vessel lid and carrier are now positioned relative to one another in this way, without the catch elements locking in one another at this point. By means of a rotational movement of the sleeve, the catch elements of the carrier and the catch elements of the lid can now be displaced relative to one another, the preliminary centering of opener and lid with respect to one another being maintained. A movement of the sleeve relative to the lid takes place until the catch elements engage and lock in one another. So that pushing the sleeve over the lid does not require additional space in the analysis system for the opener, an advantageous embodiment of the reagent vessel has a lid which has a reduced diameter in the area in which the sleeve is pushed over the lid. This is often obtained by reducing the jacket thickness of the lid, which usually has channels/notches due to manufacturing processes. Such channels or notches are generally required for the production process so that machine closure of the reagent vessels is made easier. If the outer radius of the lid is to be reduced, the formation of these channels is advantageously omitted in the upper area, so that the surface of the jacket lid in this area is smooth. The radius of the lid is thus reduced in this area by the depth of the channels. This advantageous embodiment thus also satisfies the strict space requirements of commercially standard analysis systems, as described above.

In an advantageous embodiment, the reagent vessels are connected in a cartridge to form a reagent kit. For example, such a cartridge is realized by a holding element, as is described in the prior art, for example in the document U.S. Pat. No. 5,862,934. Said document discloses a large number of reagent vessels which, at the reagent vessel neck and the closure area, are positioned relative to one another by means of a plate with corresponding recesses. The recesses provided for the reagent vessel neck and closure area are in this case adapted with an exact fit to the circumference of the reagent vessel lid, so that there is essentially no clearance between the lids and the plate. The result is that it is not possible to unscrew the lid using an opener which has to engage around the lid edge during unscrewing. Advantageously, such reagent kits can be opened using an opener according to the invention in which the catch element has a toothed structure, the reagent vessels according to the invention being closed with a lid which, as catch elements, has a complementary toothed structure on the cover plate. Engagement of the opener around the lid can thus be avoided.

The invention is explained in more detail with reference to the following examples, the embodiments being described by way of illustration.

BRIEF DESCRIPTION OF THE DRAWINGS

FIG. 1a shows an opening module of an analysis system in a perspective view.

FIG. 1b shows the side view of the opening module from FIG. 1a.

FIG. 1c shows the area of the snap-in element of the opening module on an enlarged scale.

FIG. 10.1 shows a first alternative embodiment of a snap-in element designed as a leaf spring.

FIG. 10.2 shows a second alternative embodiment of a snap-in element designed as a leaf spring.

FIG. 10.3 shows a slotted design of a snap-in element.

FIG. 10.4 shows an alternative embodiment of a snap-in element with a crossed slit.

FIG. 10.5 shows an alternative embodiment of a snap-in element designed as a clip.

FIG. 10.6 shows an alternative embodiment of the snap-in element in a pin shape.

DETAILED DESCRIPTION OF THE INVENTION

Figure 2A:
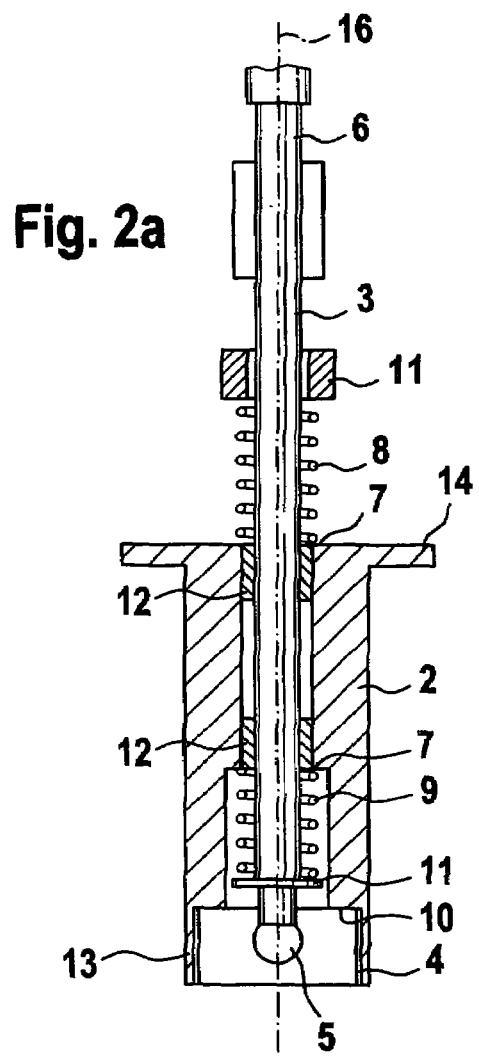
FIGS. 2a, 2b, and 2c show alternative embodiments of a centering unit arranged centrally inside a carrier.

Different views of an analysis system with a reagent cartridge opening module are shown in FIGS. 1a, 1b and 1c.

A cartridge 120 positioned in an analysis system 100 contains three reagent vessels 110, 111, two of the reagent vessels 111 being closed, while one reagent vessel 110 is in the opened state. An opening module of the analysis system 100 in FIGS. 1a and 1b is identified by reference number 1.

The reagent cartridge opening module 1 of the analysis system 100 has a carrier 2 which, at its lower end, has a catch element 4 in the form of a sleeve which is pushed over a lid 20. In the position shown, the catch element 4 is locked in a reagent vessel lid 20. The reagent vessel lid 20 has a depression 22 into which the snap-in element of the reagent cartridge opening module 1 is inserted. Snap-in elements 5 of the reagent cartridge opening module 1 and of the reagent vessel lid 20 are designed complementing one another, so that the reagent vessel lid 20 and the reagent cartridge opening module 1 can be connected to one another and the reagent vessel lid 20 clings to the reagent cartridge opening module, i.e. on the carrier 2 of the latter. A detailed description of the snap-in elements 5, designed on the carrier 2 and in the top of the reagent vessel lid 20, as shown in FIGS. 1a, 1b and 1c, is given below, and detailed alternative embodiments of the snap-in elements can be taken from FIGS. 2d, 2e, 3a, 3b, 3c and 3d and also from FIGS. 6, 7, 8 and 9.

In the illustrated position of the reagent cartridge opening module 1, it is possible in principle that the reagent cartridge opening module 1 is also used for reclosing the reagent vessels 110, 111 or that the reagent cartridge opening module 1 first discards the reagent vessel lid before the reagent cartridge opening module 1 can then be used to work on the remaining reagent vessels 110, 111.

To discard the reagent vessel lid 20, the reagent cartridge module can, for example, be positioned directly over a discard station (not shown) at which the reagent vessel lid 20 is detached from the reagent cartridge opening module 1. However, if the reagent vessel 110, 111 is to be closed again, the reagent cartridge opening module is first moved by a drive unit 112 in the Z direction to the reagent vessel 110, 111 until the reagent vessel lid 20 fits onto the vessel neck 130. By means of a rotational movement of the carrier 2 in the X-Y plane, the reagent vessel lid 20 is screwed onto the reagent vessel 110, 111, with at the same time continuation of the movement in the Z direction by an amount corresponding to the rotational movement.

FIG. 2a shows details of a reagent cartridge opening module 1 for opening reagent vessels 110, 111, with a carrier 2 in which a centering unit 3 is movably guided. The centering unit 3 is arranged centrally in the carrier 2 and extends along the carrier 2 inside a guide 12. The centering unit 3 is also connected to the carrier 2 via springs 8, 9. At its lower end, the centering unit 3 has a snap-in element 5 which is here designed in the form of a ball. The snap-in element 5 is surrounded by the catch element 4 of the carrier 2. As in FIG. 1c, the catch element 4 is designed in the form of a sleeve, the inside of the sleeve being provided with longitudinal ribs/longitudinal channels (not shown) which permit locking in a correspondingly designed reagent vessel lid 20. The springs 8, 9 of the reagent cartridge opening module 1 are in each case mounted via abutments 11, 7 of the centering unit 3 and of the carrier 2, respectively. The reagent cartridge opening module 1 is connected via a drive shaft 6 to a drive unit 112 (FIG. 1b) which can effect both a rotational movement of the centering unit 3 and also, perpendicular to this, a linear movement of the centering unit 3. In its upper area, the centering unit 3 can be designed as a hexagon. A corresponding formation of the guide 12 of the carrier 2 ensures that the centering unit 3 is fixed in terms of rotation in the carrier 2.

A rotational movement of the centering unit 3 thus automatically effects a rotation of the carrier 2. Of course, embodiments are also conceivable in which the centering unit 3 is received free in terms of rotation in the carrier 2. To achieve a rotational movement of the carrier 2, the carrier 2 is then driven directly.

Figure 2B:
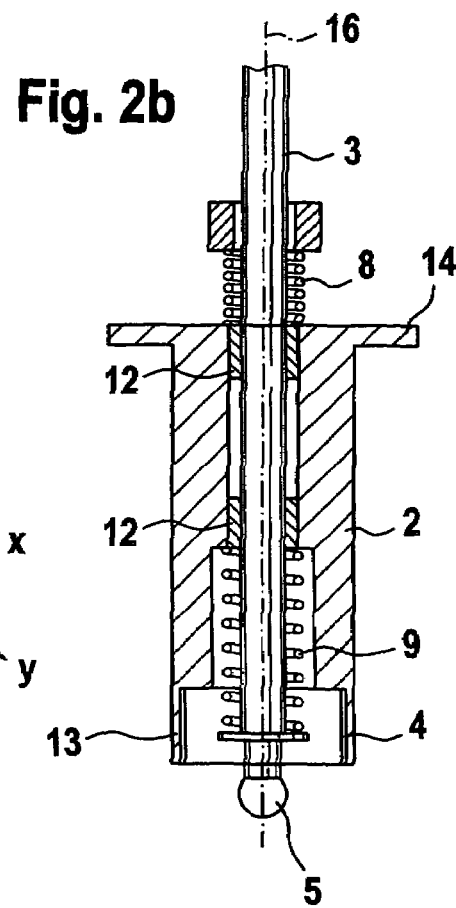

To open a reagent vessel 110, 111, a drive unit (not shown) is used to move the centering unit 3, and with it the carrier 2, in the Z direction along an axis 16 of the reagent cartridge opening module 1. When the lower end of the carrier 2 meets a cover plate of the reagent vessel lid 20, or the catch elements 43 provided there (see view in FIG. 4a), the carrier 2 generally at first sits on the cover plate of the reagent vessel lid 20. In this position, there is no exact positioning of the catch elements 4 of the carrier 2 with respect to the catch elements 43 of the reagent vessel lid 20, so that the catch elements 43 of the reagent vessel lid 20 and the catch elements 4 of the carrier 2 at first possibly do not engage in one another. When the carrier 2 lies on the reagent vessel lid 20, a continued movement of the carrier 2 in the Z direction is stopped. A continuing movement of the centering unit 3 in the Z direction has the effect that the centering unit 3 moves onwards inside the carrier 2 in the Z direction. In this way, the spring 8, which has less spring strength compared to the spring 9, is initially compressed, as is shown in FIG. 2b. At the same time, the snap-in element 5 moves in the Z direction and emerges from the sleeve 13 of the carrier 2. In doing so, the snap-in element 5 engages in connection with the corresponding snap-in element of the reagent vessel lid 20. By means of a slight rotational movement of the drive shaft 6, the snap-in element 5 secured on the centering unit 3 is then turned inside the reagent vessel lid 20, with the carrier 2 and thus the catch element 4 following the rotational movement. The rotational movement takes place until the catch elements 4 of the carrier 2 and the catch elements 43 of the reagent vessel lid 20 are correctly positioned with respect to one another and can lock in one another. The outer sleeve 13 of the carrier 2 can now engage in the catch elements 43 of the reagent vessel lid 20, the sleeve 13 of the carrier 2 being pushed with the catch elements 4 over the reagent vessel lid 20. A further rotational movement of the drive shaft 6 has the effect that the reagent vessel lid 20 follows the rotational movement, because the catch elements 4 and 43 are locked securely in terms of rotation, and thus the reagent vessel 110, 111 can be screwed open. It should be noted that the catch elements of the reagent vessel lids 20 can be designed as longitudinal ribs 43 as in FIG. 4a and also as longitudinal channels 21 as in FIG. 2e.

A slight reverse movement of the reagent cartridge opening module 1 in the Z direction is effected in order not to impede the unscrewing of the reagent vessel lid 20.

FIGS. 2b and c show the described procedure for opening a reagent vessel 110, 111. It is of course also possible to position the reagent cartridge opening module 1 relative to the reagent vessel lid 20 directly in such a way that the catch elements 4 and 43 can immediately engage in one another and a sleeve 13 of the carrier 2 is already pushed over parts of the reagent vessel lid 20 before the snap-in element 5 engages in connection with the reagent vessel lid 20.

Figure 2C:
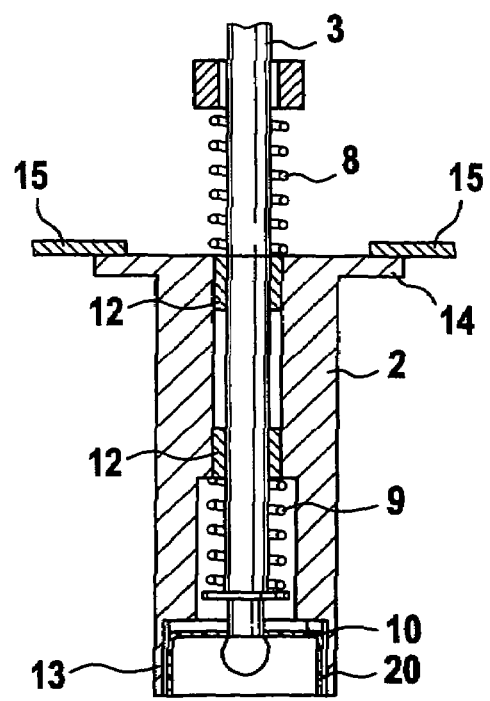

The described procedure permits preliminary centering of the centering unit 3 and thus of the carrier 2 relative to the reagent vessel lid 20, affording simplification of control processes in the analysis system 100. When the screw connection between reagent vessel 110, 111 and reagent vessel lid 20 is released by the rotational movement of the reagent cartridge opening module 1, this is moved away from the reagent vessel 110, 111 in the Z direction. The reagent vessel lid 20 can now be discarded into a waste container. To release the reagent vessel lid 20 from the reagent cartridge opening module 1, projections 14 of the carrier 2 are guided against a positionally fixed limit stop 15. If the reagent cartridge opening module 1 is moved in the Z direction, so that the carrier 2 in the analysis device abuts against the limit stop 15, only the centering unit 3 is moved inside the carrier 2, and the reagent vessel lid 20 connected to the centering unit 3 follows the movement, as is shown in FIG. 2c. The spring 9 is thus compressed, the spring 8 relaxed. The reagent vessel lid 20 follows the movement of the snap-in element 5 until the reagent vessel lid 20 inside the carrier 2 is guided against the end face 10 of the blind hole. By means of the vertical movement of the centering unit 3 relative to the carrier 2, which is held back by the limit stop 15, the centering unit 3 is pulled back relative to the carrier 2 until the reagent vessel lid 20 is pressed against the end face 10 of the blind hole, and in the further movement the snap-fit connection between reagent vessel lid 20 and reagent cartridge opening module 1 is released and the reagent vessel lid 20 falls from the sleeve 13 of the carrier 2. The reagent vessel lid 20 is now no longer attached to the reagent cartridge opening module 1, and the latter can be used for further reagent vessels 110, 111.

Figure 2D:
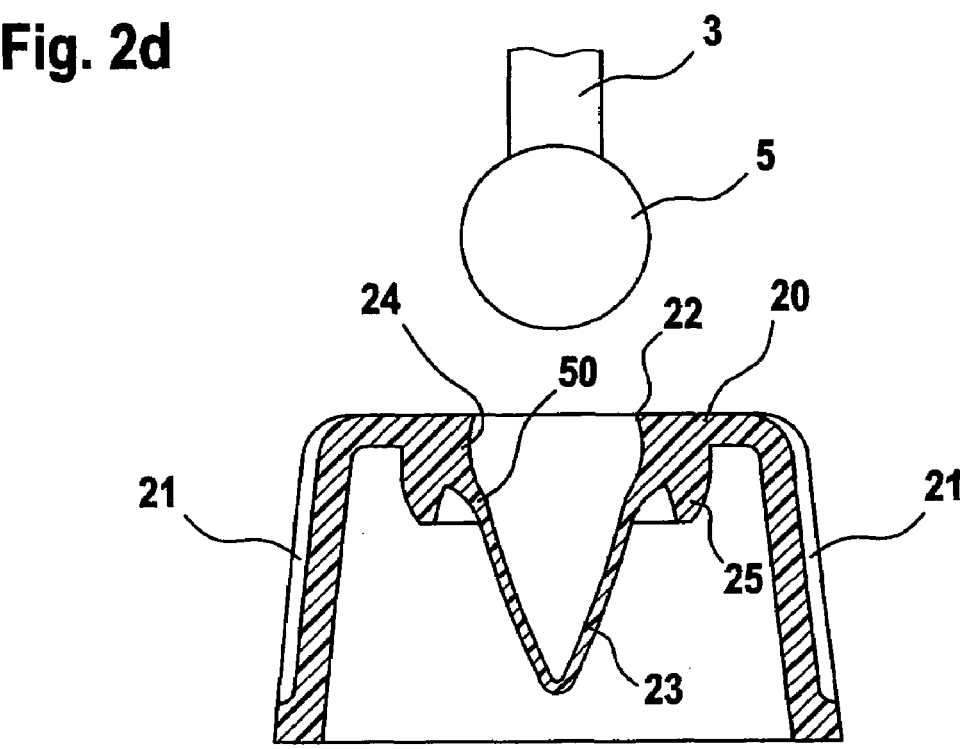
FIGS. 2d and 2e show a ball-shaped snap-in element connected to the carrier, in a position located outside a closure lid, and in a position inserted into the closure lid.
Figure 2E:
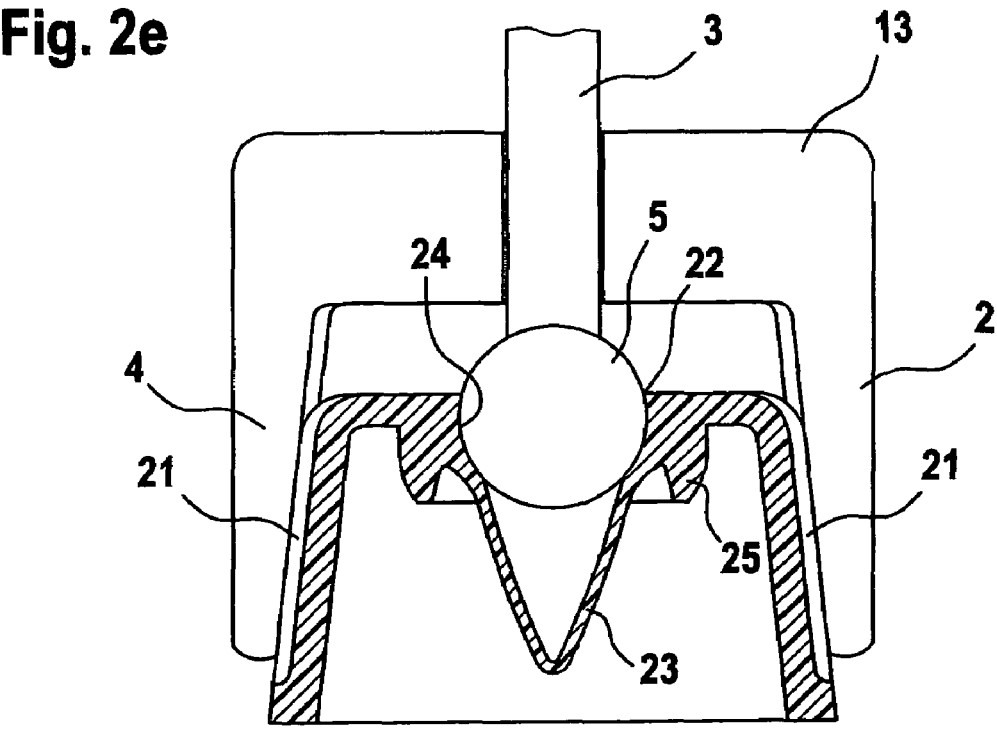

FIGS. 2d and 2e illustrate in detail the snap-fit connection, shown in FIGS. 2a and 2c, between reagent cartridge opening module 1 and reagent vessel lid 20. The snap-in element 5 of the centering unit 3 is designed in the form of a ball, as has already been shown. A correspondingly adapted reagent vessel lid 20 has a depression 22 which projects into the interior of the lid and ends in a conically shaped tip, thereby forming a snap-in element 23. Thus, in addition to its function according to the invention, a reagent vessel lid 20 designed in this way also has the possibility of being used in a method with a low sample throughput, as is described in the prior art. The reagent vessel lid 20 also has sealing lips 25 which ensure reliable sealing of the reagent vessel 110, 111 in the closed state. The outer jacket of the reagent vessel lid 20 has catch elements 43 in the form of longitudinal ribs, as have already been described in connection with FIG. 1. In an upper area 24, the depression 22 is formed by concave recesses, so as to promote a reliable snap-fit connection with the ball-shaped snap-in element 5 of the centering unit.

FIG. 2e shows the already described procedure in which the carrier 2, in its lower area, is pushed over the reagent vessel lid 20, the locking elements of the carrier 2 and of the reagent vessel lid 20 each locking in one another. At the same time, the ball-shaped snap-in element 5 snaps into the depression 22 of the reagent vessel lid 20. The suitably concave shape of the depression 22 in the upper area 24 of the reagent vessel lid 20 not only ensures a reliable snap-fit connection, but also ensures that the plastic of the reagent vessel lid 20 is not exposed to any excessive stresses when the ball-shaped snap-in element 5 is snapped into place, thereby avoiding damage to the reagent vessel lid 20. This is particularly important if the reagent vessel lid 20 is not discarded after opening, but instead is intended to be used to re-close the reagent vessel 110, 111 in the further course of the operating procedure.

FIGS. 3a, 3b, 3c and 3d show different embodiments of reagent vessel lid and snap-in element.

Figure 3A:
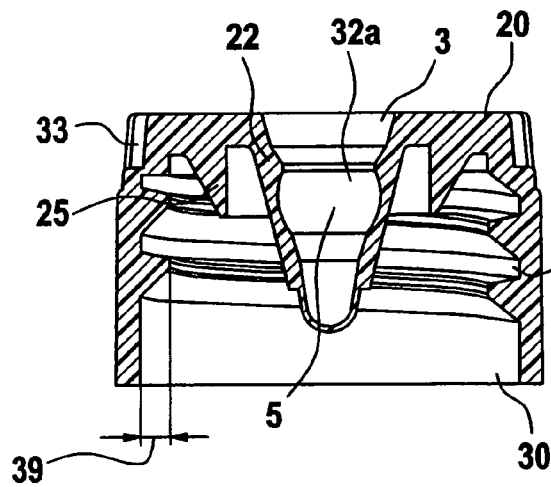
FIGS. 3a, 3b, and 3c show alternative embodiments of a reagent vessel lid.

FIG. 3a shows a cross section through a reagent vessel lid 20 which according to the invention is connected via a thread 31 to a vessel neck 130 (FIG. 5a) of a reagent vessel 30. The reagent vessel lid 20 has a thread portion, which in the use according to the invention, is connected in this thread area to the vessel neck 130 and its thread 31.

The reagent vessel lid 20 has a conically shaped depression 22. The complementary snap-in element 5 of the centering unit 3 has a conical shape which is convex in its upper area 32a. Because of the conical shape of the snap-in element 5, a preliminary centering of the reagent cartridge opening module 1 relative to the reagent vessel 111 is possible, as has already been described. The convexly shaped area 32a additionally permits a secure snap-fit connection.

To lock the reagent vessel lid 20 into the reagent cartridge opening module 1, the reagent vessel lid 20 has, in an upper area, catch elements 33 which are integrated into the cover plate of the reagent vessel lid. As has already been shown in FIG. 2, the reagent vessel lid 20 also has sealing lips 25 which ensure reliable sealing of the contents of the vessel. However, if the catch elements 43 of the reagent vessel lid 20 are not integrated into the cover plate of the reagent vessel lid 20, but instead are designed as longitudinal channels 21, as in FIG. 2d, this places demands on the reagent cartridge to satisfy the space requirement of the reagent cartridge opening module 1.

If the reagent cartridge opening module 1 is consequently used in an analysis system 100 in which there is only slight space, or no space, available for integration of the reagent cartridge opening module 1, the reagent vessel 110, 111 can be made smaller. For this purpose, it is possible, for example, to reduce the thread depth 39 of the thread 31 so as to minimize the diameter of the lid. However, any reduction of the thread depth 39 should only be to an extent which ensures a reliable sealing of the reagent vessel 110, 111 and sufficient stability of the reagent vessel lid 20 and of the sealing lips 25.

Figure 3B:
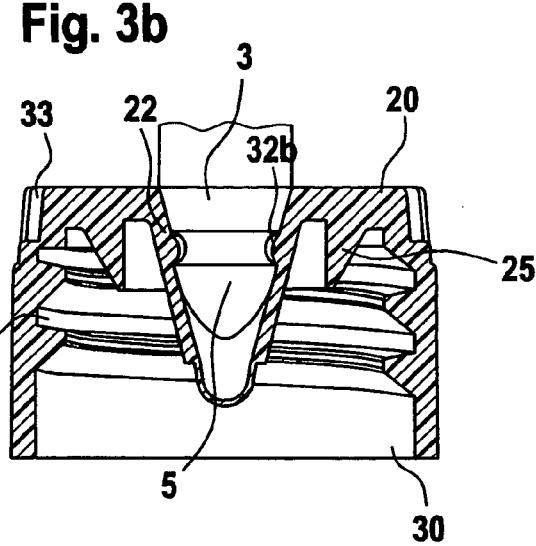

FIG. 3b shows an embodiment of the snap-in elements 5 which is complementary to that in FIG. 3a. The snap-in element 5 according to FIG. 3b is of conical shape, so that, once again, insertion of the snap-in element 5 into the depression 22 of the reagent vessel lid 20 is made easier upon application of the reagent cartridge opening module 1. The snap-in element 5 has a snap-in groove 32b as concave ring.

Figure 3C:
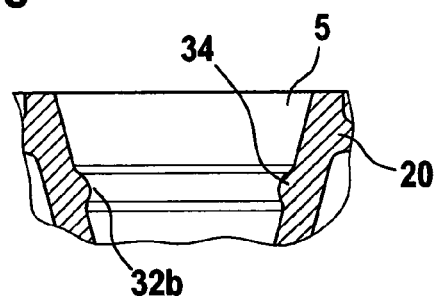
Figure 3D:
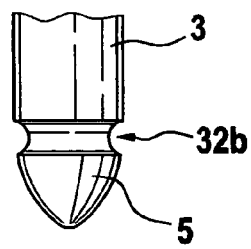
FIG. 3d shows an alternative embodiment of a snap-in element formed on the underside of the carrier.

As is shown in detail in FIG. 3c, the reagent vessel lid 20 has a corresponding protuberance 34 into which the snap-in element 5 can snap. A concavely shaped embodiment of the snap-in element 5, as shown in FIG. 3d, is of course also possible without the snap-in element 5 being made conical above the snap-in groove 32b; in the alternative embodiment of the snap-in element 5 in the view in FIG. 3d, it extends in a cylinder shape above the snap-in groove 32b.

Figure 4A:
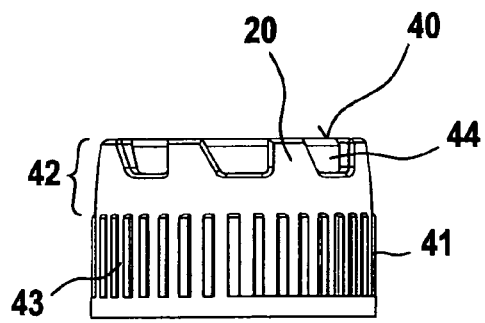
FIGS. 4a and 4b show external views of the closure lid according to the representation in FIGS. 3a, 3b and 3c.
Figure 4B:
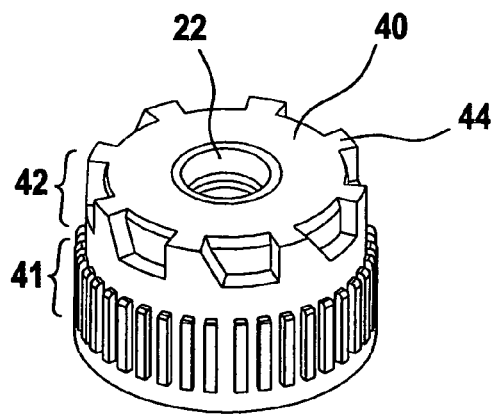

FIGS. 4a and 4b show preferred alternative embodiments of a reagent vessel lid 20. The latter has, in a cover plate 40, a depression 22 which serves as a snap-in element 5. In an upper area 42 of the jacket of the reagent vessel lid, a toothed structure 44 is formed on the cover plate 40, which toothed structure 44 can lock in a corresponding catch element of the carrier 2. To facilitate insertion of the catch elements in one another, the toothed structure 44 has an oblique configuration. In its lower area 41, the reagent vessel lid 20 has longitudinal ribs 43 which are used to screw the reagent vessel lid 20 onto the reagent vessel 110, 111 in the production process. In the upper area 42, however, the longitudinal ribs 43 are not continued, so that here the lid diameter can be reduced. Because of the reduced diameter of the lid, a sleeve 13 for example, as shown in the earlier figures, can be pushed over the reagent vessel lid 20. For the preliminary centering of the catch elements, the sleeve 13 for example is pushed over the upper area 42, the centering unit 3 additionally snapping into the reagent vessel lid 20. The catch elements 4 of the carrier 2 are then arranged in an upper area of the sleeve 13, so that they can lock into the catch elements in the cover plate 40 of the reagent vessel lid 20 when the sleeve 13 is already pushed over the area 42 of the reagent vessel lid 20. In this way, the carrier 2 can be positioned relative to the reagent vessel lid 20 by the sleeve 13 alone or in addition to the snap-fit connection. Engagement of the catch elements in one another can thus be easily ensured. By this means, catch elements of small size can also be reliably positioned with respect to one another and lock in one another, without imposing great demands on precise control of the carrier 2 or on the design of the catch elements.

Figure 5A:
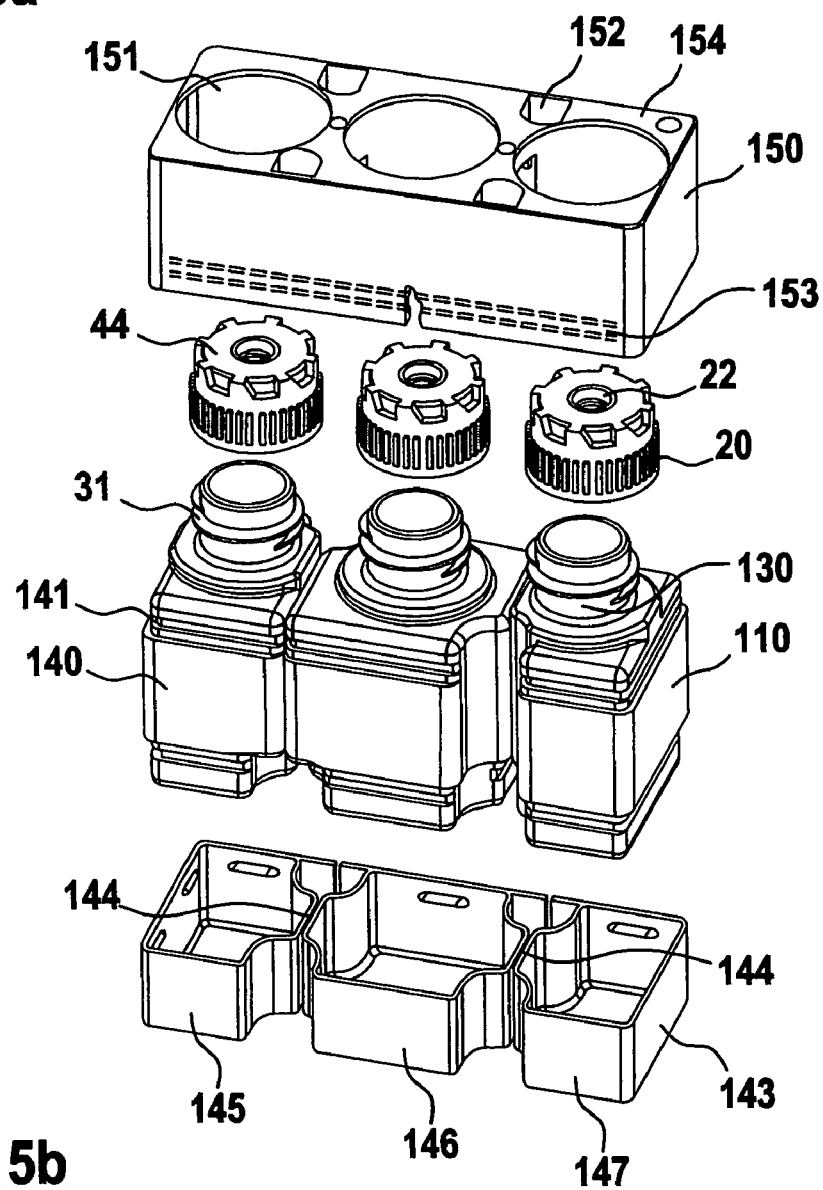
FIG. 5a shows the components of a reagent cartridge with three reagent containers.
Figure 5B:
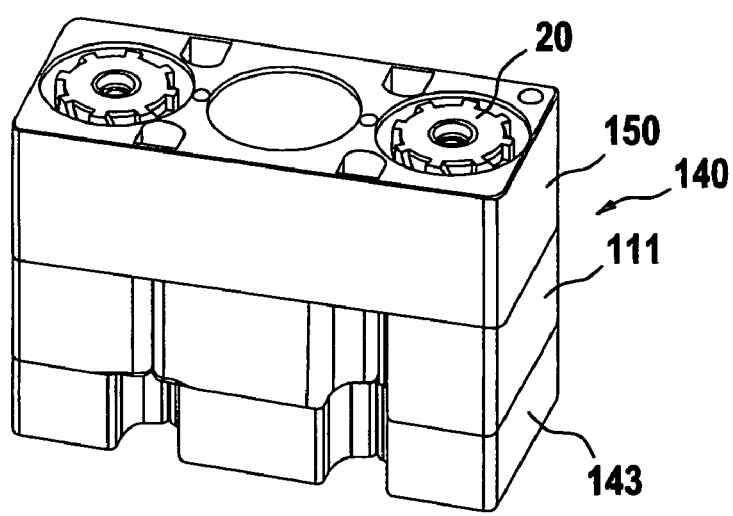
FIG. 5b shows the reagent cartridge in the assembled state.

FIGS. 5a and 5b show by way of example a plurality of reagent vessels 110, 111 which have a closure according to the invention and which are joined together to form a reagent kit. FIG. 5a shows the reagent vessels 110 in the opened state. The reagent vessels 110, 111 have a reagent vessel neck 130 with an opening for removal of a fluid contained in the reagent vessel 110, 111. The reagent vessel neck 130 also has a thread 31, so that the reagent vessel 110, 111 can be closed by screwing of the reagent vessel lid 20. The reagent vessel lids are designed analogously to those in FIG. 4 and have a toothed structure 44, which constitute the catch element of the closure cap of the reagent vessel lid 20, and have a depression 22 as snap-in element 5 of the reagent vessel lid 20, as has already been described in connection with FIG. 4.

In an area 140 of the reagent vessels 110, 111 below the reagent vessel necks 130, the reagent vessels 110, 111 have a groove 141 which interacts with a corresponding channel 153 of a top 150 and enters into a snap-fit connection with this. The top 150 is in this way firmly connected to the reagent vessel, with positioning of the reagent vessels 110, 111 relative to one another. The top 150 has up to three recesses 151 which are shaped corresponding to the circumference of the reagent vessel lid 20. In the assembled state of reagent vessel 110, 111 and top 150, a plane is formed by the cover plate 40 of the reagent vessel lid 20 and a by cover plate 154 of the top 150. The top 150 also has recesses 152 which permit transport of the reagent kit within the analysis system 100. The analysis system 100 for this purpose has gripper means which engage in the recesses 152 and permit lifting or adjustment of the reagent kit. The reagent vessels 110, 111 have, in their lower area, an obliquely shaped vessel bottom (not shown) tapering towards the center. This is intended to ensure that a pipette needle, which always sucks fluid from the center of the reagent vessel 110, 111, can also easily remove small amounts of fluid residues from the reagent vessel 110, 111. To ensure that the reagent vessels 110, 111 can be securely placed and transported in the analysis device 100 despite the obliquely shaped bottom plate, the reagent vessels 110, 111 have a bottom area 143 in which the reagent vessel 110, 111 is in each case placed and held. The bottom area 143 can be divided along partitions 144 into individual bottom parts 145, 146, 147. Each reagent vessel 110, 111 has its own clip-on bottom part 145, 146, 147. The reagent vessels 110, 111 are individually filled and screwed closed, each with its bottom part 145, 146, 147 in place, and only then mounted in a cartridge.

It would also be conceivable to clamp the reagent vessels 110, 111 and the bottom area 143 together to ensure that the reagent vessels 110, 111 are securely held inside the bottom area 143. The bottom area 143, which can also be made as one piece, has a flat bottom plate, permitting reliable placement of the reagent vessels 110, 111 in the analysis system 100. A reagent kit, in which the reagent vessels 110, 111 are joined together by means of a top 154 to form a reagent kit, is described, for example, in EP 0 692 308. The reagent kit can, for example, be made up of three reagent vessels 110, 111, as is shown in FIG. 5a, or of two reagent vessels 110, 111, as is shown in FIG. 5b. If an identical top 150 is used for reagent kits with a different number of reagent vessels 110, 111, this means that, as is shown in FIG. 5b, some of the recesses 151 for the reagent vessel lids 20 are not utilized. However, this is of no great importance for the course of an analysis procedure.

Figure 6:
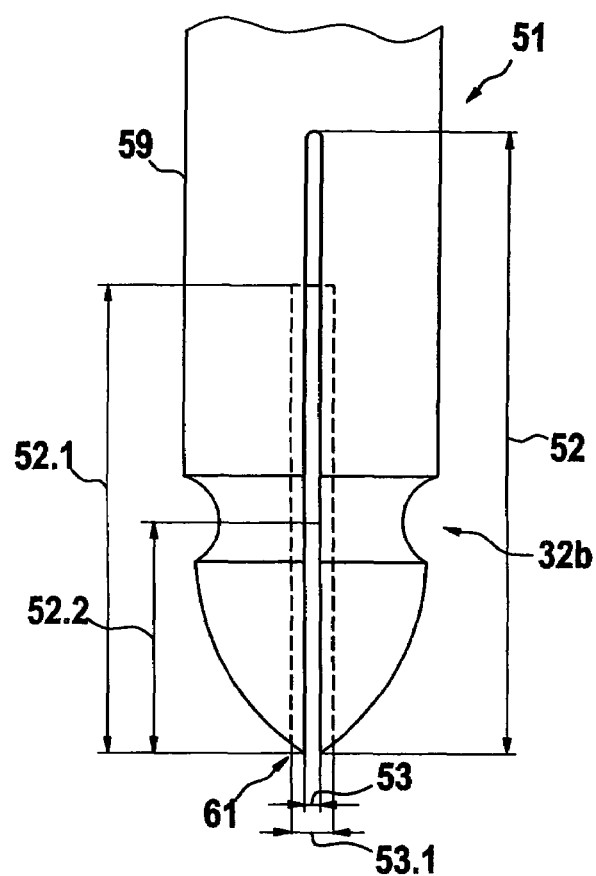
FIG. 6 shows an alternative embodiment of a slotted snap-in element.

FIG. 6 shows an alternative embodiment of a slotted snap-in element.

A slotted snap-in element 51 comprises a slit which extends parallel to the axis of symmetry and which can be designed in a first slit length 52. Depending on the desired resiliency properties of the slotted snap-in element 51, the slit can have a first length 52.1 and a further length 52.2. Reference number 53 indicates the slit width. This too can be varied, as is indicated by the greater slit width 53.1 in FIG. 6. The longitudinal slit ends at the tip 61 of the slotted snap-in element 51. On its circumferential face, it has a snap-in channel 32b which is concave and ring-shaped. Above the snap-in channel 32b, the slotted snap-in element 51 extends with a cylindrical contour 59, whereas the area of the slotted snap-in element 51 lying below the snap-in channel 32b is essentially conical.

Figure 7:
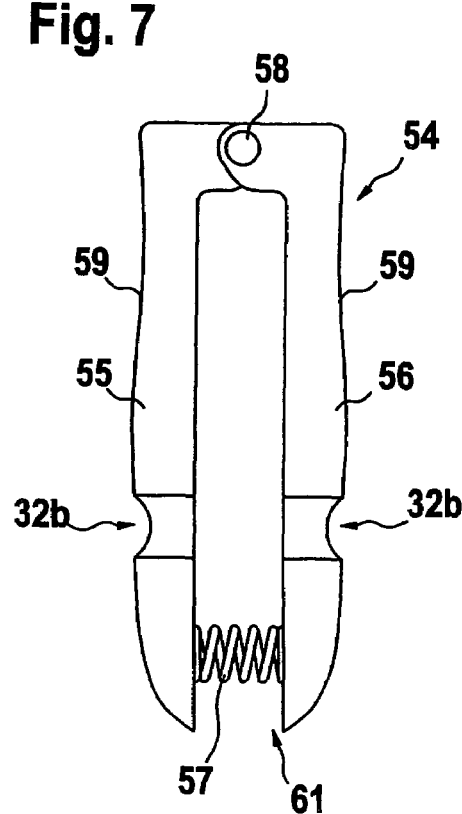
FIG. 7 shows another alternative embodiment of a snap-in element.

FIG. 7 shows a further alternative embodiment of a snap-in element.

The illustration in FIG. 7 shows a divided snap-in element 54 which has a first snap-in element half 55 and a second snap-in element half 56. The snap-in element halves 55 and 56 are connected to one another in an articulated manner at a hinge 58, and a spring 57 is arranged between the inner sides of the snap-in element halves 55, 56. The jacket surfaces of the snap-in element halves 55, 56, shown in cross section, also have a concavely shaped snap-in channel 32b. Above the snap-in channel 32b, the snap-in element halves 55, 56 extend in a cylindrical contour 59. Below the snap-in channel 32b, the snap-in element halves 55, 56 are approximately conical, tapering to a point 61.

With the alternative embodiments of snap-in elements which are shown in FIGS. 6 and 7 and which are connected to a carrier 2 (not shown here), a snap-fit connection with a reagent vessel lid 20 can be obtained which also takes account of slight production tolerances. The resiliency of the snap-in elements shown in FIGS. 6 and 7, whether provided with a longitudinal slit or designed in two parts, ensures reliable gripping of the reagent vessel lid 20.

Figure 8:
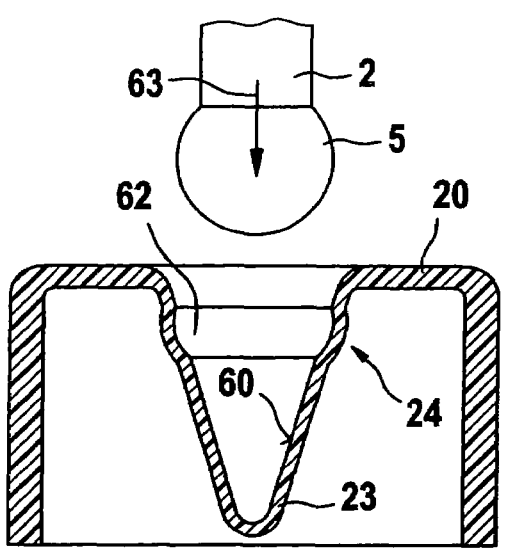
FIGS. 8 and 9 show a ball-shaped snap-in element and a cone-shaped snap-in element, respectively, which interact with a depression in a reagent vessel lid.
Figure 9:
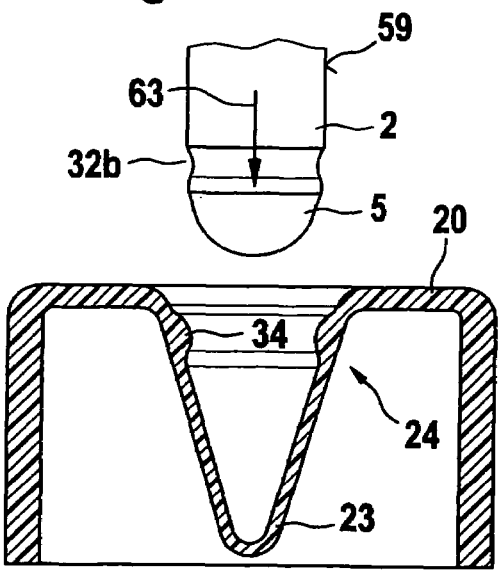

FIGS. 8 and 9 show how a ball-shaped snap-in element or, respectively, a snap-in element designed with a snap-in channel interacts with corresponding depressions inside the reagent vessel lid 20.

FIG. 8 shows a ball-shaped snap-in element 5 formed on a carrier 2 which can be moved in the direction of insertion 63 onto the reagent vessel lid 20. The reagent vessel lid 20 has the snap-in element 23 which, in the illustration in FIG. 8, is configured as a smooth cone surface or conically shaped tip 60. The ball-shaped snap-in element 5 penetrates into the snap-in element 23 and is fixed by a circumferential snap-in channel 62. The circumferential snap-in channel 62 is located in the upper area 24 of the conically shaped tip 60.

FIG. 9 shows a snap-in element 5 which is formed on a carrier 2 and on which a snap-in channel 32b is formed. The snap-in element 5 has a cylinder part 59. When the snap-in element 5 designed with the snap-in channel 32b is moved in the direction of insertion 63 towards the conically shaped tip of snap-in element 23 of the reagent vessel lid 20, the protuberance 34 in the upper area 24 of the snap-in element 23 locks into the snap-in channel 32b of the snap-in element 5, by which means a secure snap-fit connection is established.

The illustrations in FIGS. 10.1 to 10.6 show various alternative embodiments of a snap-in element used on a reagent cartridge opening module 1.

For example, the snap-in element 5 shown in FIG. 10.1 can be designed as a leaf spring 64, with a number of spring tongues 65 adjoining a cylindrical portion 59 of the carrier 2. The spring tongues 65 of the resilient snap-in element 64 can be oriented at an angle of 90° to one another, although this is not absolutely necessary. Thus, the individual spring tongues 65 could also be arranged at an angle of 120° to one another. Each of the spring tongues 65 has a recess of concave shape 32b which interacts with a complementary raised part in the wall material of the depression 22 of the reagent vessel lid 20.

FIG. 10.2 also shows a snap-in element 5, which can be designed as a slotted leaf spring 51. On the carrier 2, which merges into the resilient snap-in element 51, recesses 66 are arranged on both sides of a longitudinal slit formed in a first slit length 52. A cylinder part 59 extends below the recesses 66. This cylinder part 59 is in turn adjoined by the concave shape 32b which rounds out into a tip 61 of the snap-in element 51 designed as a leaf spring. By means of the material weakness afforded by the recesses 66 on the circumference of the carrier 2, a certain elasticity is imparted to the halves of the slotted snap-in element 51 separated by the slit 52.

FIG. 10.3 also shows a snap-in element 5 in which the recesses 66 are absent and which is designed only with a slit 68. Because of the missing recesses 66, the elasticity of the two halves of the snap-in element separated by the slit 52 is considerably less than the elasticity of the snap-in element 51 above whose cylinder part 59 the recesses 66 are located. The snap-in element 5 designed with a slit 68 also has, above the tip 61, a concave shape 32b designed as a circumferential groove.

Furthermore, FIG. 10.4 shows an alternative embodiment of a snap-in element 5 which is provided with a crossed slit 67. This means that the individual circumferential segments of the snap-in element 5 which are separated from one another by the crossed slit 67 are given an elasticity which is greater than the elasticity of the snap-in element 5 having a single slit 68. The individual segments of the snap-in element which are separated from one another by the crossed slit 67 also have, above the tip 61, a concave recess 32b which interacts with a depression 22 (not shown in FIG. 10) of the reagent vessel lid 20, as has been described in detail above.

In addition, FIG. 10.5 shows an alternative embodiment of a snap-in element 5 designed as a clip 69. The clip 69 comprises individual clip branches 71 which are arranged at an angle of approximately 90° to one another. The individual clip branches 71 also have a concave shape 32b on their outer circumference. Moreover, the clip 69 is of tubular design and has a hollow cavity 72 extending in the axial direction of the clip 69.

In addition, FIG. 10.6 shows a further alternative embodiment of a snap-in element designed as a simple pin 70, the carrier 2 having a cylinder part in which, in the lower area above the tip 61, a circumferential groove of concave shape 32b is formed.

Depending on the embodiment and on the desired stiffness, possible materials for the resilient snap-in elements 5 shown in FIGS. 10.1 and 10.2 include plastics with good slide and resiliency properties (for example POM) and metals, such as steel, or other spring materials, for example phosphor bronze. Metal materials are preferably used in the embodiments of the snap-in element 5 shown in FIGS. 10.1 and 10.2, and also for the snap-in element 5 designed as a clip in the illustration in FIG. 10.5.

LIST OF REFERENCE NUMBERS 1 reagent cartridge opening module
2 carrier
3 centering unit
4 catch element
5 snap-in element
6 drive shaft
7 first abutment
8 first spring
9 second spring
10 first projections
11 second abutment
12 guide
13 sleeve
14 second projections
15 holding device
16 axis
20 reagent vessel lid
21 longitudinal channels
22 depression
23 conical tip
24 upper area
25 sealing lips
31 thread
32a convex shape of snap-in element
32b concave shape of snap-in element
33 catch element
34 protuberance
39 thread depth
40 cover plate
42 vessel lid jacket
43 longitudinal ribs
44 toothed structures
50 soft part
51 slotted snap-in element
52 first slit length
52.1 second slit length
52.2 third slit length
53 first slit width
53.1 second slit width
54 divided snap-in element 55 first snap-in element half
56 second snap-in element half
57 spring element
58 hinge
59 cylinder part of snap-in element
60 smooth jacket surface of 23
61 tip of the snap-in element
62 peripheral channel
63 direction of insertion
64 snap-in element
65 spring tongue
66 recess
67 crossed slit
68 slit
69 clip
70 pin
71 clip branch
72 hollow cavity

What is claimed is:

1. A method for opening reagent vessels comprising:
providing a snap-fit connection between a snap-in element of a reagent cartridge opening module and a snap-in element of a reagent vessel lid without a necessity for rotation therebetween, the reagent vessel lid being connected by a screwable connection to a reagent vessel;
locking a catch element of the reagent cartridge opening module into a catch element of the reagent vessel lid, wherein the snap-in element of the reagent vessel lid and the catch element of the reagent vessel lid are permanently integrated into the reagent vessel lid and wherein the reagent vessel lid and the reagent cartridge opening module lock securely against rotation about one another;
turning the catch element of the reagent cartridge opening module, as a result of which a rotational movement of the reagent vessel lid is effected until the screwable connection between the reagent vessel lid and the reagent vessel is essentially released; and
moving the snap-in element of the reagent cartridge opening module into a direction which is essentially perpendicular to the plane of the rotational movement, wherein the reagent vessel lid clings to the snap-in element of the reagent cartridge opening module and at least partially follows the movement of the latter.

2. The method for opening reagent vessels according to claim 1, further comprising centering the snap-in element of the reagent cartridge opening module relative to the snap-in element of the reagent vessel lid before providing the snap-fit connection.

3. The method for opening reagent vessels according to claim 1 further comprising providing a carrier which, at its lower end, provides the catch element of the reagent cartridge opening module.

4. The method for opening reagent vessels according to claim 1 further comprising providing a centering unit which, at its lower end, provides the snap-in element of the reagent cartridge opening module.

5. The method for opening reagent vessels according to claim 1 further comprising:
providing a carrier which, at its lower end, provides the catch element of the reagent cartridge opening module; and
automatically positioning the catch element arranged on the carrier, relative to the center of the reagent vessel lid.

6. The method for opening reagent vessels according to claim 1 further comprising:
providing a carrier which, at its lower end, provides the catch element of the reagent cartridge opening module; and
moving the carrier and snap-in element of the reagent cartridge opening module in the direction which is essentially perpendicular to the plane of the rotational movement towards the snap-in element of the reagent vessel lid.

7. The method for opening reagent vessels according to claim 1 further comprising:
providing a carrier which, at its lower end, provides the catch element of the reagent cartridge opening module;
providing a centering unit which, at its lower end, provides the snap-in element of the reagent cartridge opening module; and
automatically matching movements of the carrier and of the centering unit to one another.

8. The method for opening reagent vessels according to claim 1 further comprising:
providing a carrier which, at its lower end, provides the catch element of the reagent cartridge opening module;
providing a centering unit inside the carrier, the centering unit, at its lower end, provides the snap-in element of the reagent cartridge opening module;
automatically positioning the catch element arranged on the carrier, relative to the center of the reagent vessel lid; and
moving the carrier and centering unit in the direction which is essentially perpendicular to the plane of the rotational movement towards the snap-in element of the reagent vessel lid to lock the catch element of the reagent cartridge opening module into the catch element of the reagent vessel lid and to provide the snap-fit connection.

9. The method for opening reagent vessels according to claim 1 further comprising providing relative movement between the snap-in element of the reagent cartridge opening module and the catch element of the reagent cartridge opening module to release the snap fit connection.

10. The method for opening reagent vessels according to claim 1 further comprising:
providing a carrier which, at its lower end, provides the catch element of the reagent cartridge opening module; and
providing a drive unit which is operably coupled to the carrier to turn the catch element.

11. The method for opening reagent vessels according to claim 1 further comprising:
providing a carrier which, at its lower end, provides the catch element of the reagent cartridge opening module;
providing a centering unit which, at its lower end, provides the snap-in element of the reagent cartridge opening module;
automatically matching movements of the carrier and of the centering unit to one another; and
triggering relative movement between the carrier and the centering unit upon bringing bearing surfaces of the carrier up against a positionally fixed limit stop.

12. The method for opening reagent vessels according to claim 1 further comprising:
providing a carrier which, at its lower end, provides the catch element of the reagent cartridge opening module;
providing a centering unit inside the carrier, the centering unit, at its lower end, provides the snap-in element of the reagent cartridge opening module;
automatically positioning the catch element arranged on the carrier, relative to the center of the reagent vessel lid;

moving automatically together the carrier and centering unit in the direction which is essentially perpendicular to the plane of the rotational movement towards the snap-in element of the reagent vessel lid; and triggering relative movement between the carrier and the centering unit upon bringing bearing surfaces of the carrier up against a positionally fixed limit stop.

13. The method for opening reagent vessels according to claim 1, further comprising implementing said method in an analysis system.

14. A method for opening reagent vessels comprising:

providing a reagent cartridge opening module having a carrier which, at its lower end, provides a catch element, and a centering unit inside the carrier, the centering unit, at its lower end, provides a snap-in element;

centering the snap-in element of the reagent cartridge opening module relative to a snap-in element of a reagent vessel lid, the reagent vessel lid being connected by a screwable connection to a reagent vessel;

moving automatically together the carrier and centering unit in an essentially perpendicular direction towards the snap-in element of the reagent vessel lid;

providing a snap-fit connection between the snap-in element of the reagent cartridge opening module and the snap-in element of the reagent vessel lid without a necessity for rotation therebetween;

locking the catch element of the carrier into a catch element of the reagent vessel lid, wherein the snap-in element of the reagent vessel lid and the catch element of the reagent vessel lid are permanently integrated into the reagent vessel lid and wherein the reagent vessel lid and the reagent cartridge opening module lock securely against rotation about one another;

turning the catch element of the carrier, as a result of which a rotational movement of the reagent vessel lid is effected until the screwable connection between the reagent vessel lid and the reagent vessel is essentially released;

moving the snap-in element of the reagent cartridge opening module in a direction which is essentially perpendicular to the plane of the rotational movement, wherein the reagent vessel lid clings to the snap-in element of the reagent cartridge opening module and at least partially follows the movement of the latter; and triggering relative movement between the carrier and the centering unit upon bringing bearing surfaces of the carrier against a positionally fixed limit stop to release the snap-fit connection.

15. The method for opening reagent vessels according to claim 14, further comprising providing a drive unit which is operably coupled to the carrier to turn the catch element.

16. The method for opening reagent vessels according to claim 14, further comprising implementing said method in an analysis system.

17. The method for opening reagent vessels according to claim 14, further comprising providing the snap-in element of the reagent cartridge opening module with a concave shape.

18. The method for opening reagent vessels according to claim 14, further comprising providing the snap-in element of the reagent cartridge opening module with a convex shape.

19. The method for opening reagent vessels according to claim 14, further comprising providing the snap-in element of the reagent cartridge opening module with a conical shape.

20. The method for opening reagent vessels according to claim 14, further comprising providing the catch element of the reagent cartridge opening module with a tooth structure.

21. The method for opening reagent vessels according to claim 14, further comprising providing the reagent vessel lid with teeth on the cover plate.

22. The method for opening reagent vessels according to claim 14, further comprising providing the reagent vessel lid with a tapered cone portion.

23. The method for opening reagent vessels according to claim 14, further comprising providing the snap-in element of the reagent cartridge opening module with a depression which has a groove on the inside.

24. The method for opening reagent vessels according to claim 14, further comprising providing the snap-in element of the reagent cartridge opening module with a depression which has a protuberance on the inside.

25. The method for opening reagent vessels according to claim 14, further comprising providing the snap-in element of the reagent cartridge opening module as hinged snap-in element halves.

26. The method for opening reagent vessels according to claim 14, further comprising providing the snap-in element of the reagent cartridge opening module as a slotted snap-in element that is designed conically or cylindrically above a snap-fit groove and which has a tapered end.

* * * * *

UNITED STATES PATENT AND TRADEMARK OFFICE
CERTIFICATE OF CORRECTION

| | | |
|---|---|---|
| PATENT NO. | : 7,666,357 B2 | Page 1 of 1 |
| APPLICATION NO. | : 10/778586 | |
| DATED | : February 23, 2010 | |
| INVENTOR(S) | : Stephan Sattler | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1195 days.

Signed and Sealed this
Fifth Day of June, 2012

David J. Kappos
*Director of the United States Patent and Trademark Office*